United States Patent
Trubetskoy et al.

(10) Patent No.: US 7,045,356 B2
(45) Date of Patent: *May 16, 2006

(54) PROCESS FOR GENERATING MULTILAYERED PARTICLES

(75) Inventors: Vladimir Trubetskoy, Middleton, WI (US); Jon A. Wolff, Madison, WI (US); James E. Hagstrom, Middleton, WI (US); Vladimir G. Budker, Middleton, WI (US); So Chun Wong, Oregon, WI (US); Jason Klein, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 178 days.

This patent is subject to a terminal disclaimer.

(21) Appl. No.: 10/795,679

(22) Filed: Mar. 8, 2004

(65) Prior Publication Data

US 2004/0203154 A1    Oct. 14, 2004

Related U.S. Application Data

(62) Division of application No. 10/265,024, filed on Oct. 4, 2002, now Pat. No. 6,740,336.

(51) Int. Cl.
   *C12N 15/88* (2006.01)
(52) U.S. Cl. ...................................... 435/458; 424/450
(58) Field of Classification Search ................ 435/458; 424/450

See application file for complete search history.

(56) References Cited

U.S. PATENT DOCUMENTS

2001/0004636 A1 *  6/2001  Monohan et al. .............. 514/44
2002/0061861 A1 *  5/2002  Herweijer et al. ............ 514/44

\* cited by examiner

*Primary Examiner*—James Ketter
(74) *Attorney, Agent, or Firm*—Mark K. Johnson; Kirk Ekena

(57) ABSTRACT

We describe a process for generating multilayer particles comprising condensing a polymer with an oppositely charged polymer to form a particle and sequentially adding oppositely charged polymers to the particle forming at least three layers of polymers. The process is used to form a composition for delivering a biologically active compound to a cell.

18 Claims, 5 Drawing Sheets

RH-DNA / Alexa-lPEI, no sucrose

Buffer, 2.5% sucrose pGlu + 5% sucrose

Buffer, 7.5% sucrose lPEI, 10% sucrose

Buffer, 12.5% sucrose pGlu, 15% sucrose

Buffer, 17.5% sucrose lPEI, 20% sucrose

Buffer, 22.5% sucrose

Density cushion, 40% metrizamide

A.

B.

C.

PROCESS FOR GENERATING MULTILAYERED PARTICLES

CROSS-REFERENCE TO RELATED APPLICATIONS

This application is a divisional of application Ser. No. 10/265,024, filed Oct. 4, 2002, now U.S. Pat. No. 6,740,336.

BACKGROUND

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to cells is the use of DNA-polycation complexes. It has been shown that cationic proteins like histones and protamines or synthetic polymers like polylysine, polyarginine, polyornithine, DEAE dextran, polybrene, and polyethylenimine may be effective intracellular delivery agents.

Preparation of polycation-condensed polyanion (such as DNA) particles is of particular importance for non-viral gene therapy. Optimal transfection activity in vitro and in vivo can require an excess of polycation molecules. However, the presence of a large excess of polycations is potentially toxic to cells and tissues. Moreover, the non-specific binding of cationic particles to cells as well as serum components hinders specific cellular targeting. Positive charge can also have an adverse influence on biodistribution of the complexes in vivo.

Layer-by-layer polymeric assemblies, based on electrostatic interactions of polyanions and polycations, have found applications in different fields of materials science. Such assemblies are fabricated by consecutive deposition of alternating polycation and polyanion layers on a surface of interest by incubation in dilute aqueous solutions of corresponding polyion. However, this method is applicable only to macroscopic substrates since it requires separation of the substrate from excess polyion after addition of each layer. The formation of such assemblies has been demonstrated on planar macrosurfaces [Decher, G., Science, 277, 1232–1237 (1997)] and latex microspheres [Donath, E., Sukhorukov, G B, Caruso, F., Davis, S A, Möhwald, H. Angew. Chem. 110, 2324–2327 (1998)]. This approach is not amenable to fabrication of multilayer coating of smaller particles, such as condensed DNA complexes, due to the problem of separation of the particle from excess polyion after deposition of each layer.

It is known that polycation/polyanion complexes formed in low salt aqueous solution assume morphology of small spherical particles of submicron size [Dautzenberg, H, Hartmann, J, Grunewald, S, Brand, F. Ber. Bunsenges. Phys. Chem. 100, 11024–1032 (1996)]. Recently we have demonstrated that electrostatic complexes <100 nm in diameter can be build around small particles of polycation-condensed DNA [Trubetskoy V S, Loomis A, Hagstrom J E, Budker V G, Wolff J A, Nucleic Acids Res. 27, 3090–3095 (1999); Trubetskoy V S, Slattum P M, Hagstrom J E, Wolff J A, Budker V G. Anal. Biochem. 267:309–313, (1999)]. However, formation of these complexes—without separation from excess polyion during addition of each layer—results in generation of large quantities of blank complexes. The blank particles are formed from interaction of the excess polycation and polyanion and do not contain DNA. Nevertheless, the DNA-containing particles were shown to be useful as gene transfer agents [Prov. Appl. Ser. No. 60/093, 153].

SUMMARY

Figure 1:
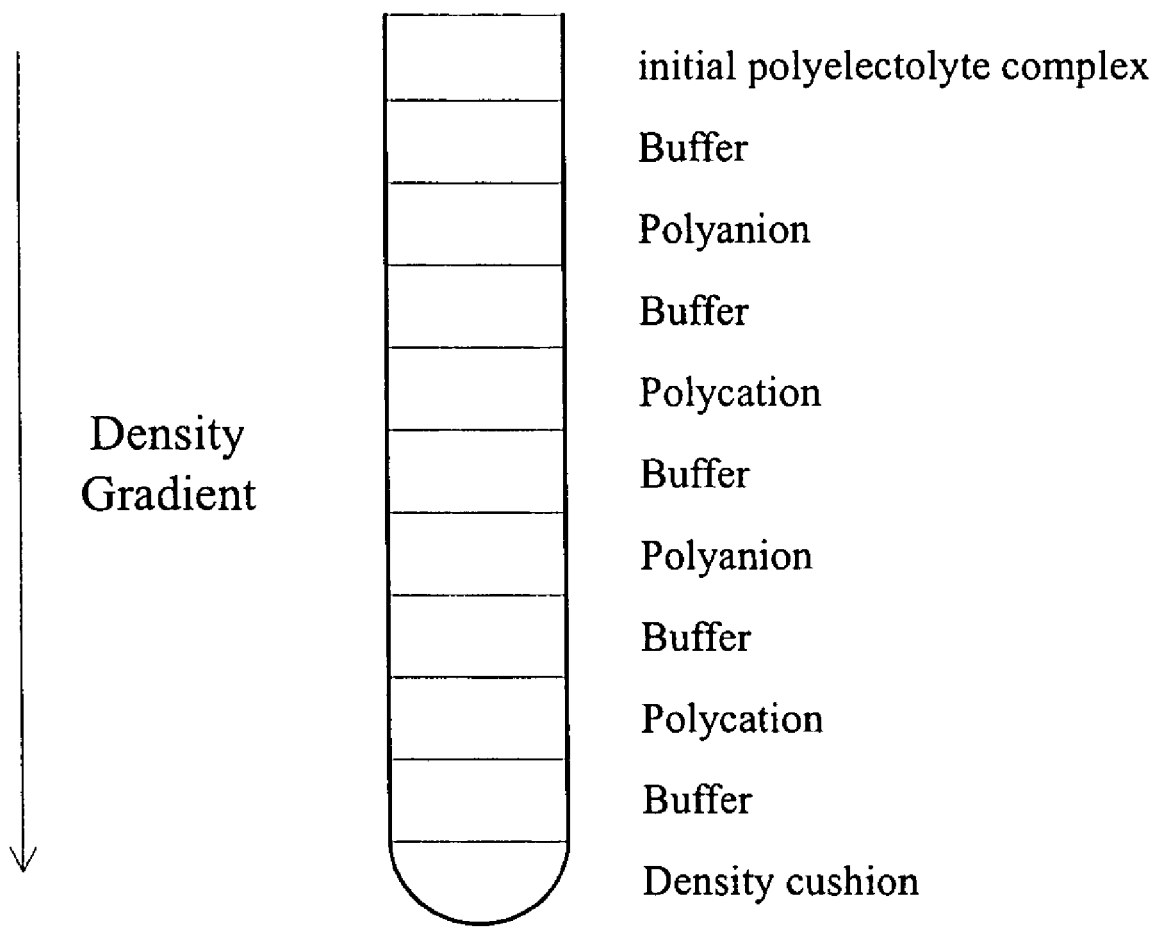
FIG. 1. Diagram showing a density gradient setup for the formation of multilayered particles. The diagram illustrates alternating polyanion, polycation, and buffer layers. Lowest density is at the top of the gradient and highest density is at the bottom of the gradient. The number of layers and composition of each layer may be altered for a specific purpose.

This invention pertains to the formation of multilayered polyelectrolyte complexes containing various macromolecules or compounds (i.e. polymers, nucleic acids, proteins, drugs, etc.). The formation of multilayered complexes provides a method for increasing the overall amount of polymer in each individual complex. When the polymer provides a specific functionality to the complex, the increasing amount of polymer present in the successive layers allows for increased overall functionality of the complex. The inclusion of more layers (i.e. multilayering) allows for increased amounts of polymers containing functionalities comprising: ligands, membrane active compounds, endosomal lytic activity, hydrophilicity, hydrophobicity, biologically active molecules, cell targeting signals, protonateable groups, etc.

In a preferred embodiment, we describe a process for fabrication in solution of nanometer-scale multilayer complexes wherein alternating layers are composed of polyanions and polycations comprising: condensing a polyanion with a polycation in a solution to form a core complex, sequentially adding alternating solutions of polycations and polyanions, and forming the multilayer complex. Any polyion in the core complex or subsequent layers may be or may include as a component a biologically active compound or functional group. A preferred core polyanion is nucleic acid.

In a preferred embodiment, we describe a process for fabrication in solution of nanometer-scale multilayer complexes wherein alternating layers are composed of polyanions and polycations comprising: condensing a polyanion with a polycation in a solution to form a core complex, sedimenting by centrifugation the core complex through an appropriate density gradient consisting of alternating layers of polyanions, polycations and buffer in increasing concentrations of density gradient-forming solute, and forming the multilayer complex. Any polyion in the core complex or subsequent layers may be or may include as a component a biologically active compound or functional group. A preferred core polyanion is nucleic acid. A preferred density gradient is a step gradient consisting of increasing concentrations of sucrose (Example 1, FIG. 1), but other gradients that do not cause aggregation, dissociation or decondensation of the polymers or complexes is acceptable. The gradient and polyions are chosen such that the complexes of interest sediment through the gradient when centrifuged at an appropriate speed more readily than free polyions or blank particles. Blank complexes are those complexes that do not contain the core complex.

In a preferred embodiment, the process can be used to form nanometer-scale complexes that contain more polycation than is present in the core complex. In another preferred embodiment, the complex may contain more polycation than is present in the core complex but has a surface charge that is negative, i.e. a negative $\zeta$-potential. Such particles are recharged by the addition of a polyanion as the final layer.

In a preferred embodiment, we describe a composition for delivering a biologically active compound to a cell comprising: a multilayer complex consisting of alternating layers of polycation and polycation wherein one or more of the layers is or includes as a component a biologically active compound. A preferred biologically active compound is a nucleic acid, such as DNA or RNA. In one aspect of the invention, the multilayered polyelectrolyte complexes can be used to deliver biologically active compounds to cells in vitro, in vivo, in situ or ex vivo.

In a preferred embodiment, we describe a process for delivering a biologically active polyanion to a cell comprising: condensing the biologically active polyanion with a polycation in a solution to form a core complex, sedimenting by centrifugation the core complex through a density gradient consisting of alternating layers of polyanion, polycation and buffer in increasing concentrations of solute, forming a multilayer complex, collecting the multilayer complex, associating the multilayer complex with a cell, and delivering the biologically active polyanion to the cell. A preferred biologically active polyanion is nucleic acid. The multilayer complex may have a positive or negative $\zeta$-potential or surface charge. The multilayered polyelectrolyte complexes can be used to deliver biologically active compounds to cells in vitro, in vivo, in situ or ex vivo.

In a preferred embodiment, centrifugation of condensed DNA complexes through a sucrose step gradient consisting of alternating polycation-containing and polyanion-containing layers results in fabrication of multilayered electrostatic assemblies with condensed DNA at the core and does not contain the admixture of non-DNA-containing blank complexes. Other density gradients and density gradient-forming solutes may also be used.

In a preferred embodiment, a process is described for delivering a complex to a mammalian cell, comprising: forming a complex having multiple alternating layers of polyanion and polycation and inserting the complex into a mammal.

In a preferred embodiment, a polyion may be modified with neutral hydrophilic polymers for steric stabilization of the whole complex.

In another preferred embodiment, a polyion layer in a complex may be covalently or noncovalently attached to the same or a different polyion layer in the complex in order to crosslink the layers. Bifunctional molecules may be added that crosslink the complex. A polyanion may contain groups that covalently or noncovalently attach to a polycation. Alternatively, a polycation may contain groups that covalently or noncovalently attach to a polyanion. Crosslinking can occur during formation of the multilayer complex or after formation of the multilayer complex.

Reference is now made in detail to the preferred embodiments of the invention, examples of which are illustrated in the accompanying drawings.

DETAILED DESCRIPTION

We describe methods for the fabrication of multilayer polyelectrolyte complexes (particles). In one method, a core complex is first generated by condensation of a polyion with a polyion of opposite charge in a low salt buffer such as water. The amounts of polyions are chosen so that small, <100 nm, particles are formed. The precise amounts are determined empirically for different polyions but are typically related to charge density of the polyions (charge per molecular weight). Successive layers of alternating polyanion and polycation are then added sequentially to the complex. The amounts of polyion are chosen such that upon addition of each layer the particles remain small, <100 nm, and the surface of the complex is recharged without causing aggregation (see example 5). Polyanions of lower charge density, such as succinylated PLL and poly(glutamic acid), do not decondense DNA in DNA/polycation complexes, even when added in 20-fold charge excess to polycation. Further studies have found that displacement effects are salt-dependent. In the absence of salt such the complexes may exist indefinitely. Measurement of the $\zeta$-potential of DNA/PLL particles during titration with SPLL revealed the change of particle surface charge at approximately the charge equivalency point. Using this method, the surface charge of a polyelectrolyte complex can be reversed and thus the complex can be "recharged".

Figure 2:
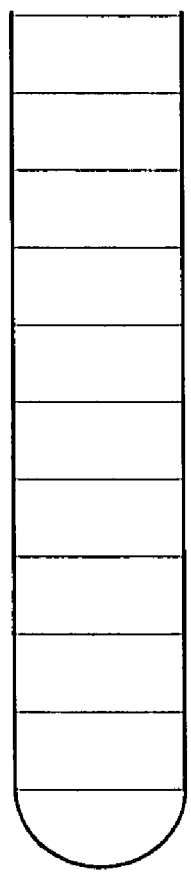
FIG. 2. Fabrication of condensed DNA particles formed with alternating layers of poly(ethyleneimine) (lPEI) and poly(glutamic acid) (pGlu). The diagram illustrates a sucrose step gradient for the formation of six-layer DNA-containing particles containing three lPEI layers. Sucrose density and polyion type are shown for each layer.

In another method a core complex is first fabricated as described above, for example with DNA and lPEI. This core complex is then applied to the top of a density gradient wherein the gradient contains alternating layers of polyanions and polycations in increasing concentrations of a density gradient-forming solute, such as sucrose (FIGS. 1 and 2). The solute is chosen such that its presence does not cause aggregation or dissociation of the complexes. This method takes advantage of the higher density of condensed nucleic acid-containing particles compared with polyanion/polycation complexes that do not contain nucleic acid. The DNA-containing particles sediment through the gradient during centrifugation at appropriate rpm while particles that do not contain DNA, blank particles, float in the gradient. The bottom layer of the gradient may be a cushion, such a 40% metrizamide, such that the DNA-containing particles float on the surface of the metrizamide and are not pelleted in the bottom of the tube. This method allows the fabrication of nanometer-scale multilayer complexes that contain the core complex, without contamination of excess blank particles.

By forming multilayer particles, more of a given polyion—or functional molecule attached to a polyion—is incorporated into the complex. This quality can improve delivery of a biologically active compound to a cell. For instance, multilayer DNA/lPEI particles—which contain more lPEI within the complex—are more efficient transfection vectors than compositions that contain similar amounts of lPEI, but with less lPEI incorporated into DNA-containing complexes and more excess lPEI free in solution.

Multilayer particles with a negative surface charge (i.e. complexes in which the outermost layer is composed of polyanions), may be used to enhance delivery. Negative surface charge on the particles may reduce non-specific interactions with cells and serum proteins [Wolfert et al. Hum. Gene Therapy 7:2123–2133 (1996); Dash et al., Gene Therapy 6:643–650 (1999); Plank et al., Hum. Gene Ther. 7:1437–1446 (1996); Ogris et al., Gene Therapy 6:595–605 (1999); Schacht et al. Brit. Patent Application 9623051.1 (1996)]

A wide a variety of polyanions can be used to recharge the DNA/polycation particles comprising: succinylated PLL, succinylated PEI (branched), polyglutamic acid, polyaspartic acid, polyacrylic acid, polymethacrylic acid, polyethylacrylic acid, polypropylacrylic acid, polybutylacrylic acid, polymaleic acid, dextran sulfate, heparin, hyaluronic acid, polysulfates, polysulfonates, polyvinyl phosphoric acid, polyvinyl phosphonic acid, copolymers of polymaleic acid, polyhydroxybutyric acid, acidic polycarbohydrates, DNA, RNA, negatively charged proteins, pegylated derivatives of above polyanions, pegylated derivatives carrying specific ligands, block and graft copolymers of polyanions, any hydrophilic polymers (PEG, poly(vinylpyrrolidone), poly (acrylamide), etc), and other water-soluble polyanions Any polyion in the multilayer complex may be cleavable or labile. Cleavable means that a chemical bond between atoms is broken. Labile also means that a chemical bond between atoms is breakable.

Polyions within the complex may also be crosslinked to enhance stability of the complex or to enable attachment of a ligand or signal or other functional group to be attached. Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule. A polyion in a complex can be covalently or noncovalently attached to another polyion in the complex using a variety of chemical reactions.

The multilayer particles may be used to delivery a biologically active compound to a cell that is in vitro or in vivo. The biologically active compound is delivered to a cell if the biologically active compound becomes associated with the cell. The biologically active compound may can be on the membrane of the cell or inside the cytoplasm, nucleus, or other organelle of the cell.

For delivery in vivo, biologically active compound-containing multilayer particles may be delivered intravascualry, intrarterially, intravenously, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes.

Definitions

Density gradient means increasing density of a solute.

Successive layer means a layer at a higher density in a density gradient.

Multilayer is at least 3 layers of alternating charged polymers.

A polyion (or polyelectrolyte), is a polymer possessing charge, i.e. the polymer contains a group (or groups) that has either gained or lost one or more electrons.

A polycation can be a polymer possessing net positive charge, for example poly-L-lysine hydrobromide or a histone. The polymeric polycation can contain monomer units that are charge positive, charge neutral, or charge negative, however, the net charge of the polymer must be positive. A polycation also can be a non-polymeric molecule that contains two or more positive charges.

A polyanion can be a polymer containing a net negative charge, for example polyglutamic acid. The polymeric polyanion can contain monomer units that are charge negative, charge neutral, or charge positive, however, the net charge on the polymer must be negative. A polyanion can also be a non-polymeric molecule that contains two or more negative charges.

The term polyion includes polycations, polyanions, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. Biologically active compounds may be selected from the group comprising: pharmaceuticals, proteins, peptides, polypeptides, hormones, cytokines, antigens, viruses, oligonucleotides, and nucleic acids.

The term nucleic acid, or polynucleotide, is a term of art that refers to a polymer containing at least two nucleotides. Natural nucleotides contain a deoxyribose (DNA) or ribose (RNA) group, a phosphate group, and a base. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. Nucleotides are the monomeric units of nucleic acid polymers. Polynucleotides with less than 120 monomeric units are often called oligonucleotides. The term polynucleotide includes deoxyribonucleic acid (DNA) and ribonucleic acid (RNA). Natural polynucleotides have a ribose-phosphate backbone. An artificial or synthetic polynucleotide is any polynucleotide that is polymerized in vitro and contains the same or similar bases but may contain a backbone of a type other than the natural ribose-phosphate backbone. These backbones include, but are not limited to: PNAs (peptide nucleic acids), phosphorothioates, phosphorodiamidates, morpholinos, and other variants of the phosphate backbone of natural polynucleotides.

DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. Anti-sense polynucleotides, siRNA, and ribozymes are polynucleotides that interferes with the function of DNA and/or RNA. Interference may result in suppression of expression. The polynucleotide can also be a sequence whose presence or expression in a cell alters the expression or function of cellular genes or RNA. In addition, nucleic acid polymers may be single, double, triple, or quadruple stranded.

A delivered nucleic acid can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A nucleic acid can be delivered to a cell to express an exogenous nucleotide sequence, to inhibit, eliminate, augment, or alter expression of an endogenous nucleotide sequence, or to affect a specific physiological characteristic not naturally associated with the cell. Nucleic acids may contain an expression cassette coded to express a whole or partial protein, or RNA. An expression cassette refers to a natural or recombinantly produced nucleic acid that is capable of expressing a gene(s). The term recombinant as used herein refers to a nucleic acid molecule that is comprised of segments of polynucleotide joined together by means of molecular biological techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette may include, but is not limited to, transcriptional enhancers, locus control regions, non-coding sequences, introns, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences.

The nucleic acid may contain sequences that do not serve a specific function in the target cell but are used in the generation of the nucleic acid. Such sequences include, but are not limited to, sequences required for replication or selection of the nucleic acid in a host organism.

A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by hybridization, multistrand nucleic acid formation, homologous recombination, gene conversion, or other yet to be described mechanisms.

The term gene generally refers to a nucleic acid sequence that comprises coding sequences necessary for the production of a therapeutic nucleic acid (e.g., ribozyme) or a polypeptide or precursor. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses both cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the messenger RNA (mRNA) transcript. The mRNA functions during translation to specify the sequence or order of amino acids in a nascent polypeptide. The term non-coding sequences also refers to other regions of a genomic form of a gene including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotide) or at distant sites (more than 10,000 nucleotides). These non-coding sequences influence the level or rate of transcription and translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, and immunogenicity. One example of covalent modification of nucleic acid involves the action of LabelIT reagents (Mirus Corporation, Madison, Wis.).

As used herein, the term gene expression refers to the process of converting genetic information encoded in a gene into RNA (e.g., mRNA, rRNA, tRNA, or snRNA) through transcription of a deoxyribonucleic gene (e.g., via the enzymatic action of an RNA polymerase), and for protein encoding genes, into protein through translation of mRNA. Gene expression can be regulated at many stages in the process. Up-regulation or activation refers to regulation that increases the production of gene expression products (i.e., RNA or protein), while down-regulation or repression refers to regulation that decrease production. Molecules (e.g., transcription factors) that are involved in up-regulation or down-regulation are often called activators and repressors, respectively.

The process of delivering a nucleic acid to a cell has been commonly termed transfection or the process of transfecting and also it has been termed transformation. The term transfecting as used herein refers to the introduction of foreign nucleic acid or other biologically active compound into cells. The biologically active compound could be used to produce a change in a cell that can be therapeutic. The delivery of nucleic acid for therapeutic and research purposes is commonly called gene therapy. The delivery of nucleic acid can lead to modification of the genetic material present in the target cell. The term stable transfection or stably transfected generally refers to the introduction and integration of exogenous nucleic acid into the genome of the transfected cell. The term stable transfectant refers to a cell which has stably integrated foreign nucleic acid into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of foreign nucleic acid into a cell where the foreign nucleic acid does not integrate into the genome of the transfected cell. The foreign nucleic acid persists in the nucleus of the transfected cell. The foreign nucleic acid is subject to the regulatory controls that govern the expression of endogenous genes in the chromosomes. The term transient transfectant refers to a cell which has taken up foreign nucleic acid but has not integrated this nucleic acid.

A transfection reagent is a compound or compounds that bind(s) to or complex(es) with oligonucleotides and polynucleotides, and mediates their entry into cells. The transfection reagent also mediates the binding and internalization of oligonucleotides and polynucleotides into cells. Examples of transfection reagents include, but are not limited to, cationic lipids and liposomes, polyamines, calcium phosphate precipitates, histone proteins, polyethylenimine, and polylysine complexes. It has been shown that cationic proteins like histones and protamines, or synthetic cationic polymers like polylysine, polyarginine, polyornithine, DEAE dextran, polybrene, and polyethylenimine may be effective intracellular delivery agents. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via cell targeting signals that bind to receptors on or in the cell. For example, cationic liposomes or polylysine complexes have net positive charges that enable them to bind to DNA or RNA.

Functional group. Functional groups include cell targeting signals, nuclear localization signals, compounds that enhance release of contents from endosomes or other intracellular vesicles (releasing signals), reactive groups and other compounds that alter the behavior or interactions of the compound or complex to which they are attached.

Cell targeting signals are any signals that enhance the association of the biologically active compound with a cell. These signals can modify a biologically active compound such as drug or nucleic acid and can direct it to a cell location (such as tissue) or location in a cell (such as the nucleus) either in culture or in a whole organism. The signal may increase binding of the compound to the cell surface and/or its association with an intracellular compartment. By modifying the cellular or tissue location of the foreign gene, the function of the biologically active compound can be enhanced. The cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. A variety of ligands have been used to target drugs and genes to cells and to specific cellular receptors. The ligand may seek a target within the cell membrane, on the cell membrane or near a cell. Binding of ligands to receptors typically initiates endocytosis. Ligands include agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active compound to certain parts of the cell.

Nuclear localizing signals enhance the targeting of the pharmaceutical into proximity of the nucleus and/or its entry into the nucleus during interphase of the cell cycle. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. Other NLS peptides have been derived from the hnRNP A1 protein, nucleoplasmin, c-myc, etc.

Many biologically active compounds, in particular large and/or charged compounds, are incapable of crossing biological membranes. In order for these compounds to enter cells, the cells must either take them up by endocytosis, i.e., into endosomes, or there must be a disruption of the cellular membrane to allow the compound to cross. In the case of endosomal entry, the endosomal membrane must be disrupted to allow for movement out of the endosome and into the cytoplasm. Either entry pathway into the cell requires a disruption of the cellular membrane. Compounds that disrupt membranes or promote membrane fusion are called membrane active compounds. These membrane active compounds, or releasing signals, enhance release of endocytosed material from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides. The control of when and where the membrane active compound is active is crucial to effective transport. If the membrane active agent is operative in a certain time and place it would facilitate the transport of the biologically active compound across the biological membrane. If the membrane active compound is too active or active at the wrong time, then no transport occurs or transport is associated with cell rupture and cell death. Nature has evolved various strategies to allow for membrane transport of biologically active compounds including membrane fusion and the use of membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Another functional group comprises compounds, such as polyethylene glycol, that decrease interactions between molecules and themselves and with other molecules. Such groups are useful in limiting interactions such as between serum factors and the molecule or complex to be delivered [Wolfert et al. Hum. Gene Therapy 7:2123–2133 (1996), Ogris et al., Gene Therapy 6:595–605 (1999)].

Hydrophobic groups indicate in qualitative terms that the chemical moiety is water-avoiding. Typically, such chemical groups are not water soluble, and tend not to form hydrogen bonds.

Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

EXAMPLES

1. Density gradient for the formation of multilayer particles: A core complex, such as a condensed polyanion/polycation complex, is made in solution without sucrose and layered on top of a density gradient. The density gradient contains alternating layers of polyanion, polycation and buffer in increasing density layers as shown in FIG. 1. Buffer solutions in between polyelectrolyte-containing steps are used to avoid polyanion/polycation mixing and thus formation of insoluble interpolyelectrolyte complexes on the border between adjacent gradient steps. Centrifugation is than used to sediment the core complex through the layers of the gradient. As the complex sediments through a polyion containing layer, the polyion is deposited on the complex to form an additional layer on the particle. Polyion that is not deposited on the particle remains in the layer during centrifugation and does not sediment though the gradient. Thus, excess blank particles are not formed. The composition of each layer may be altered for each specific purpose. The number of layers may also be altered for each specific purpose.

2. Formation of multilayer DNA-containing particles: To demonstrate the fabrication method, we used rhodamine-labeled DNA (Rh-DNA) [Trubetskoy, V. S., Budker, V. G., Slattum, P. M., Hagstrom, J. E., Wolff, J. A. (1999) *Anal. Biochem.* 267, 309–313] and linear poly(ethyleneimine) (lPEI, Polysciences) labeled with Alexa-633 N-hydroxysuccinimide ester (Alexa, Molecular Probes). Multilayered complexes were prepared during centrifugation of initial condensed DNA through the consecutive sucrose density gradient steps containing alternating polyion (polycation or polyanion) or buffer (see FIG. 2).

The starting DNA/lPEI complexes in buffer without sucrose were placed on top of the step sucrose gradient. Buffer solutions in between polyelectrolyte-containing steps were used to avoid polyanion/polycation mixing and thus formation of insoluble interpolyelectrolyte complexes on the border between adjacent sucrose gradient steps.

To demonstrate formation of multilayered DNA/polycation/polyanion complexes the several gradients were assembled and centrifuged using a Beckman L80 ultracentrifuge and an SW-41 rotor. The initial Rh-DNA/Alexa-lPEI (50 µg/100 µg) complexes were formed in 10 mM HEPES, pH 7.5 buffer. Polyglutamic acid (pGlu) and lPEI (60 µg each) were added to the corresponding sucrose steps (FIG. 2). This setup results in the formulation of multilayer complexes having three layers of lPEI with two layers of pGlu surrounding the condensed DNA core.

Three gradients were assembled:
 1). Labeled Alexa-lPEI was used only in the formation of initial Rh-DNA/Alexa-lPEI complex (0% sucrose);
 2). Alexa-lPEI was used in the formation of initial complex and first polycation layer placed in 10% sucrose step; and,
 3). Alexa-lPEI was used in initial complex formation and first (10% sucrose) and second (20% sucrose) polycation layers.

Unlabeled lPEI was used in all other layers. All three gradients were centrifuged at 35,000 rpm for 0.5 hr and fractionated in 1 ml fractions starting from the bottom of the tube. Rh-DNA-containing complexes were isolated from the surface of the metrizamide density cushion. NaCl was added to the isolated complexes up to the concentration of 2.5 M in order to dissociate the complexes before registering the visible spectra.

Figure 3:
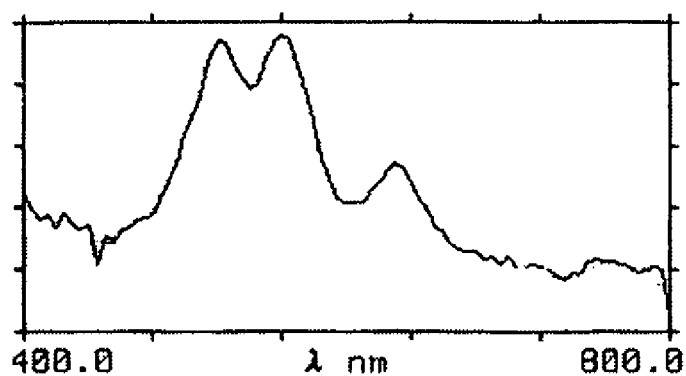
FIG. 3. Visible spectra of Rhodamine-DNA/Alexa 633-lPEI/pGlu six-layer particles containing: a) one labeled lPEI layer, b) two labeled lPEI layers, or c) three labeled lPEI layers.
Figure 3:
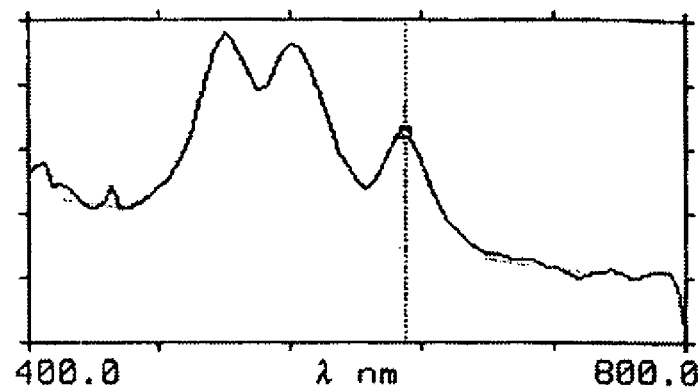
Figure 3:
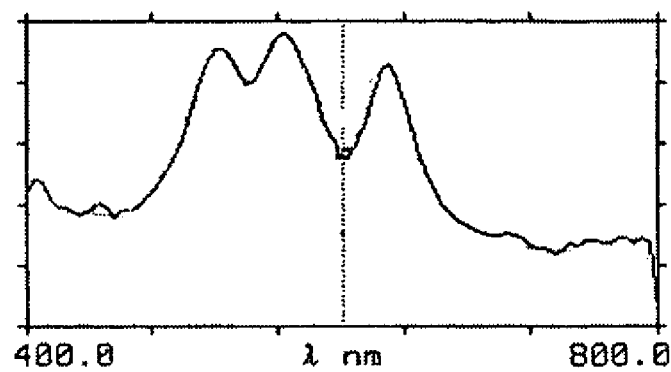
Figure 4:
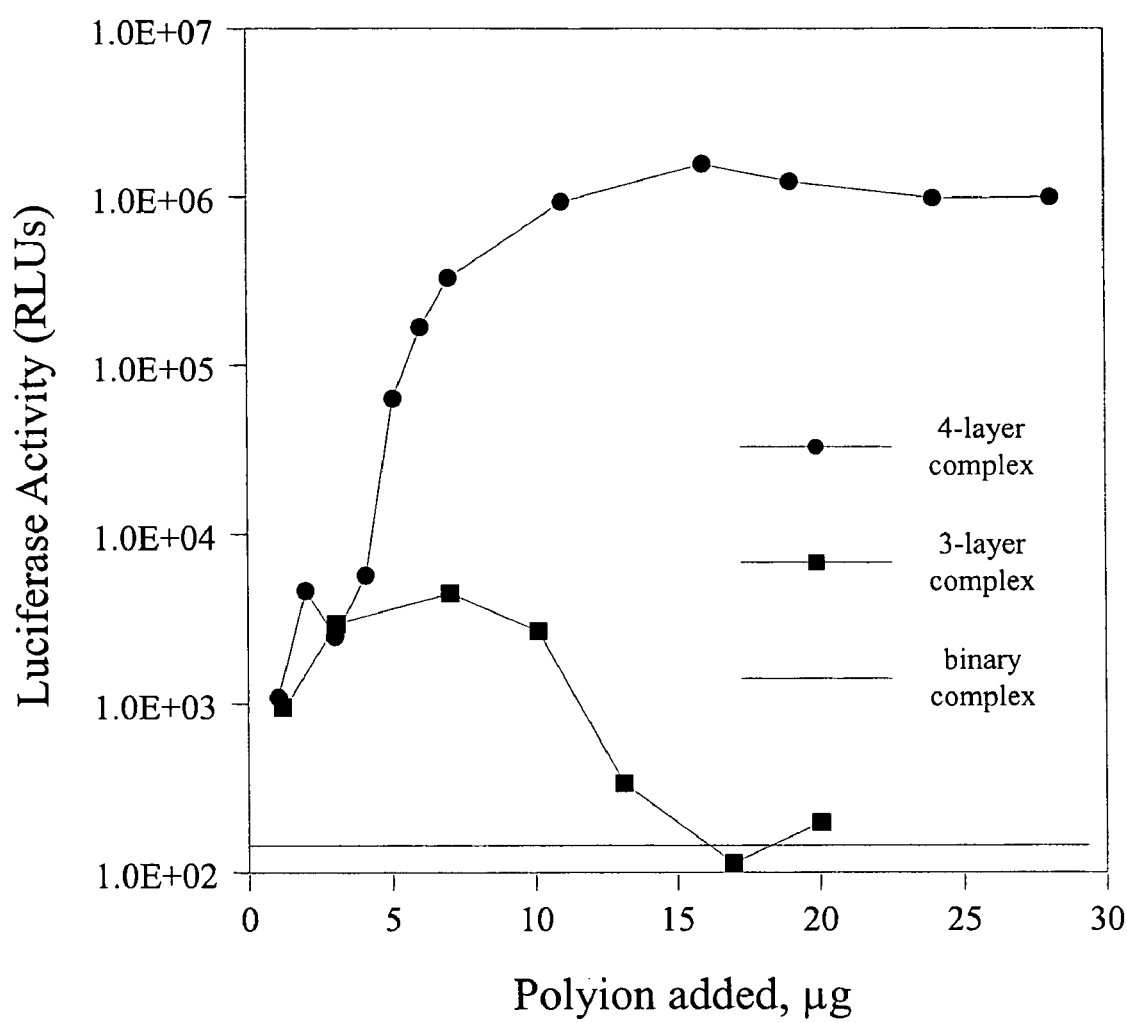
FIG. 4. Gene transfer activity of multilayer complexes in Hepa cells. Gene transfer activity of two-layer, three-layer and four-layer particles containing Luciferase encoding plasmid DNA are shown. X-axis represents that amount of polyion in the outermost layer.

The stoichiometry of the multilayer complexes was deduced from measurung the ratio of Rh-DNA (540 nm) and Alexa-lPEI(630 µm) peak intensities in the spectrum of the isolated complex. FIG. 3 demonstrates the spectra of the samples 1, 2 and 3 with one, two and three layers of Alexa-lPEI (third major peak in each sprectum). The Alexa-lPEI-to-Rh-DNA intensity ratio was found to be 0.48, 0.65 and 0.98 for samples 1,2 and 3 respectively which is proportional to the number of labeled lPEI layers of the final complex.

3. In vitro gene transfer activity of multilayer polyplex complexes: Complex formation was performed in water by consecutive addition of polyion to previously-formed particles. The initial binary (core) complex was formed by mixing 5 µg DNA with 3 µg lPEI. Three-layer complexes, DNA/lPEI/MC510, were formed by addition of varying amounts of anionic polymer MC510 (Mirus proprietary compound) to the binary complex. Four-layer complexes, DNA/lPEI/MC510/lPEI, were formed by addition of varying amounts of lPEI to DNA (5 µg)/lPEI (3 µg)/MC510 (20 µg) three-layer complexes. For each complex formulation, 1 µg DNA per well was added to Hepa cells in vitro grown in 6-well (35 mm well) plates. Complexes were incubated with cells in serum-free Opti-MEM at 37° C. for 4 h. Media was then replaced with DMEM+10% fetal calf serum and cells were incubated for an additional 20 h. Luciferase activity was then measured in cell lysates.

Gene transfer activity of four-layer complexes significantly exceeded transfer activity of the three-layer complexes which, in turn, exceeded transfer activity of core DNA/lPEI binary complexex. No activity was observed for the core DNA/lPEI complexes.

4. In vitro gene transfer activity of multilayer polyplex complexes: Complexes containing varying number of layers composed of DNA, lPEI and pGlu were prepared as described above. Amounts of polymers were chosen to keep the complexes small, <100 nm as determined by light diffraction. The complexes were prepared in water by sequential addition of pGlu and lPEI layers around the core DNA/lPEI complex.

1) 5 mg DNA;
2) 5 μg DNA/4 μg lPEI/5 μg pGlu;
3) 5 μg DNA/4 μg lPEI/5 μg pGlu/5 μg lPEI/6 μg pGlu;
4) 5 μg DNA/4 μg lPEI/5 μg pGlu/5 μg lPEI/6 μg pGlu/7 μg lPEI/8 μg pGlu

Figure 5:
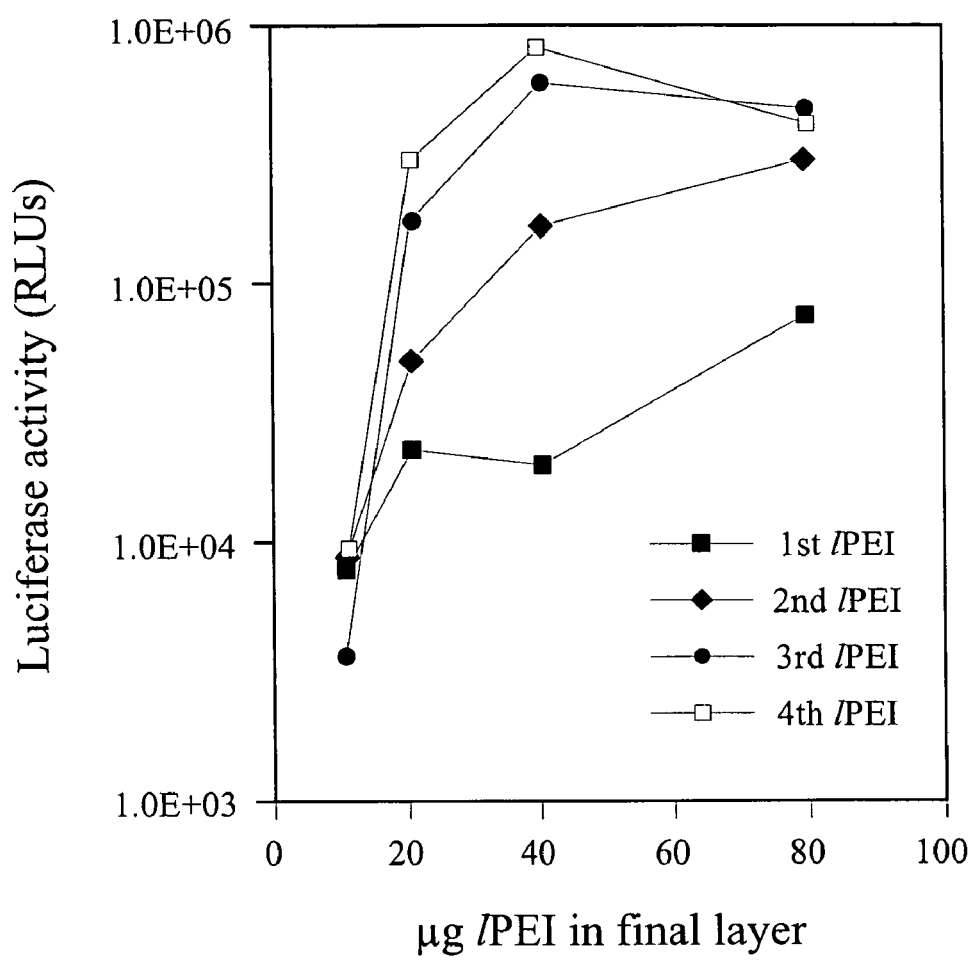
FIG. 5. Gene transfer activity of multilayer DNA/lPEI/pGlu complexes in HeLa cells. Gene transfer activity for particles containing 1, 2, 3, or 4 lPEI layers are shown. X-axis represents the amount of lPEI in the outermost layer.

To each of these particles was added varying amounts of lPEI, again in water. Particles containing 1 μg DNA were used to transfect HeLa cells as described above for Hepa cells. Luciferase activity was assay after 24 h to determine transfection efficiency (FIG. 5). Particles containing more layers exhibited increased transfection efficiency. The efficiency increases began to plateau between 3 and 4 lPEI layers in this experiment.

REFERENCES

Dash et al., Gene Therapy 6:643–650 (1999)
Dautzenberg, H, Hartmann, J, Grunewald, S, Brand, F. Ber. Bunsenges. Phys. Chem. 100, 11024–1032 (1996)
Decher, G., Science, 277, 1232–1237 (1997)
Donath, E., Sukhorukov, G B, Caruso, F., Davis, S A Möhwald, H. Angew. Chem. 110, 2324–2327 (1998)
Ogris et al., Gene Therapy 6:595–605 (1999)
Plank et al., Hum. Gene Ther. 7:1437–1446 (1996)
Prov. Appl. Ser. No. 60/093,153
Schacht et al. Brit. Patent Application 9623051.1 (1996)
Trubetskoy V S, Loomis A, Hagstrom J E, Budker V G, Wolff J A, Nucleic Acids Res. 27, 3090–3095 (1999)
Trubetskoy V S, Slattum P M, Hagstrom J E, Wolff J A, Budker V G. Anal. Biochem. 267:309–313, (1999)
Trubetskoy, V. S., Budker, V. G., Slattum, P. M., Hagstrom, J. E., Wolff, J. A. (1999) *Anal. Biochem.* 267, 309–313
Trubetskoy V S, Loomis A, Slattum P M, Hagstrom J E, Budker V G, Wolff J A. Bioconjug Chem. July–August 1999; 10(4):624–628.
Wolfert et al. Hum. Gene Therapy 7:2123–2133 (1996)

We claim:

1. A process for delivering a polynucleotide to a cell comprising:
   a) condensing a first polyanion with a polycation to form a particle;
   b) adding a second polyanion to the particle to form a complex wherein at least one of the polyanions is the polynucleotide;
   c) crosslinking the second polyanion to the polycation; and,
   d) contacting the cell with the complex.

2. The process of claim 1 wherein condensing the first polyanion with the polycation forms a positively charged particle.

3. The process of claim 1 wherein the complex is charge neutral.

4. The process of claim 1 wherein the complex is negatively charged.

5. The process of claim 1 wherein the complex is positively charged.

6. The process of claim 1 wherein a functional group is associated with the complex.

7. The process of claim 6 wherein the functional group is selected from the list consisting of: cell targeting signals, nuclear localization signals, membrane active compounds and interaction modifiers.

8. A process for delivering a polynucleotide to a cell comprising:
   a) adding a solution containing a polynucleotide to a solution containing an excess of polycation wherein the polynucleotide and the polycation interact to form a particle;
   b) adding a solution containing an excess of polyanion to the particle wherein the particle and the polyanion interact to form a complex; and,
   c) contacting the cell with the complex.

9. The process of claim 8 wherein the excess of polycation and the excess of polyanion are removed from the solution prior to contacting the complex with the cell.

10. The process of claim 8 wherein the polyanion is crosslinked to the polycation.

11. A complex for delivering a polynucleotide to a cell, comprising:
    three or more layers of polyions of alternating charge wherein at least one of the polyions is the polynucleotide.

12. The complex of claim 11 wherein the complex comprises a condensed polycation/polyanion core complex.

13. The complex of claim 12 wherein the complex is charge neutral.

14. The complex of claim 12 wherein the complex is negatively charged.

15. The complex of claim 12 wherein the complex is positively charged.

16. The complex of claim 11 wherein at least one polyion layer is crosslinked to a successive polyion layer.

17. The complex of claim 11 wherein a functional group is associated with the complex.

18. The complex of claim 17 wherein the functional group is selected from the list consisting of: cell targeting signal, nuclear localization signal, membrane active compound and interaction modifier.

* * * * *